United States Patent [19]

Mathys

[11] Patent Number: 4,685,923
[45] Date of Patent: Aug. 11, 1987

[54] HIP JOINT SOCKET

[75] Inventor: Robert Mathys, Bettlach, Switzerland

[73] Assignee: Robert Mathys Co., Bettlach, Switzerland

[21] Appl. No.: 837,891

[22] Filed: Mar. 10, 1986

Related U.S. Application Data

[63] Continuation-in-part of Ser. No. 689,572, Jan. 7, 1985, abandoned.

[30] Foreign Application Priority Data

Jan. 11, 1984 [CH] Switzerland ............... 121/84

[51] Int. Cl.⁴ ............................................. A61F 2/34
[52] U.S. Cl. ..................................................... 623/22
[58] Field of Search ...................... 623/20, 21, 22, 23; 128/92 C, 92 CA

[56] References Cited

FOREIGN PATENT DOCUMENTS

| 0058753 | 9/1982 | European Pat. Off. ............. 623/22 |
| 2807289 | 8/1979 | Fed. Rep. of Germany ........ 623/22 |
| 2857297 | 2/1980 | Fed. Rep. of Germany ........ 623/22 |
| 2225924 | 12/1974 | France ................................... 623/22 |

Primary Examiner—Richard J. Apley
Assistant Examiner—David J. Isabella
Attorney, Agent, or Firm—Werner W. Kleeman

[57] ABSTRACT

An artificial hip joint socket made of plastic is intended to be installed in the pelvic bone without bone cement. The hip joint socket comprises a ribbed outer surface which permits good engagement of the bone tissue as well as two anchor plugs protruding from the outer surface which are intended to be inserted into corresponding bores in the bone. The angle which the plugs form with the socket surface deviate from the angle which the bores form with the socket surface by about 5° in order to effect a predetermined prestressing action which restrains the hip joint socket in position. Furthermore, the hip joint socket comprises at least two barb-like anchor flaps on its outer surface which either lie opposite one another or mutually include an angle of between 120° and 150°. A good seating of the hip joint socket in the bone is ensured by these flaps even immediately after insertion of the hip joint socket. Thus, even if the anchor plugs offer insufficient retention for any reason, the employment of screws or dowels can be completely or partially foregone.

5 Claims, 5 Drawing Figures

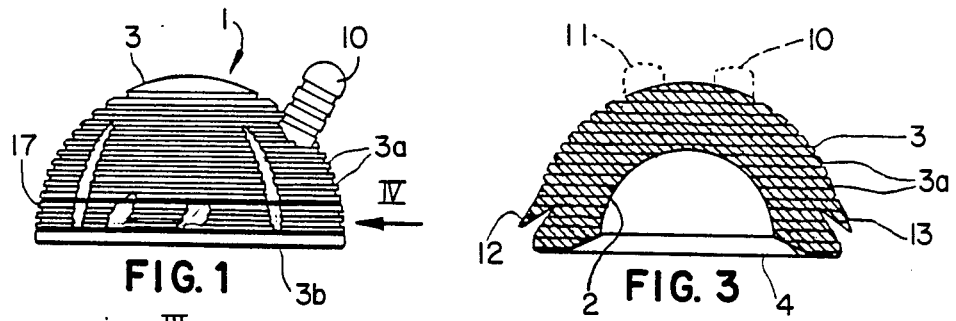
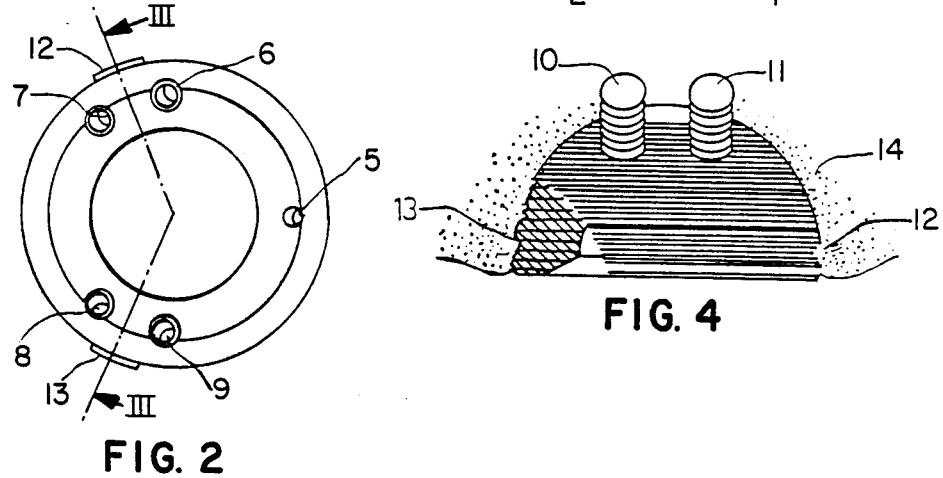
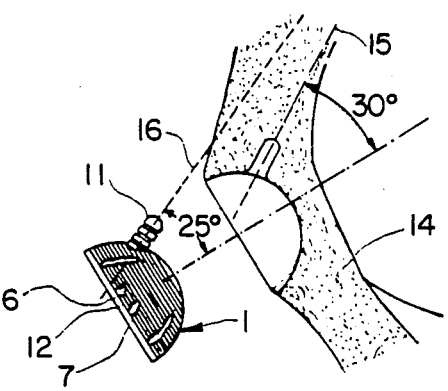

4,685,923

HIP JOINT SOCKET

CROSS-REFERENCE TO RELATED APPLICATIONS

This application is is a continuation-in-part application of my commonly assigned, co-pending U.S. patent application Ser. No. 06/689,572, filed on Jan. 7, 1985, entitled "Hip Joint Socket", now abandoned. This application is also related to my commonly assigned, co-pending U.S. patent application Ser. No. 06/689,566, filed Jan. 7, 1985 and entitled: "Plastic Joint Socket", now abandoned.

BACKGROUND OF THE INVENTION

The present invention broadly relates to artificial surgical joints and, more specifically, pertains to a new and improved construction of a plastic hip joint socket for adhesive-free installation.

Generally speaking, the plastic hip joint socket of the present invention is intended for adhesive-free installation and comprises a socket body having an outer surface and two anchor plugs protruding from the outer surface.

The present invention is a further development of and an improvement on the hip joint socket intended for adhesive-free installation according to the Swiss Patent No. 544,544. The present invention thus relates to an artificial hip joint socket made of plastic material and comprising two preferably substantially parallel anchor plugs or pins protruding from the outer surface of the socket.

SUMMARY OF THE INVENTION

It is a primary object of the present invention to provide a new and improved construction of an artificial hip joint socket made of plastic which can be reliably installed without the use of bone cement or adhesive.

A further significant object of the present invention aims at providing a new and improved construction of an artificial hip joint socket of the character described which is relatively simple in construction and design, extremely economical to manufacture, highly reliable in operation, not readily subject to breakdown or malfunction and requires a minimum of surgical and remedial attention.

Now in order to implement these and still further objects of the invention, which will become more readily apparent as the description proceeds, the artificial hip joint socket of the present invention is manifested by the features that it comprises at least two supplementary barb-like anchor flaps integrally formed upon the outer surface of the hip joint socket. These integrally formed barb-like anchor flaps, which are cut-out of the body of the hip joint socket, are advantageously deflected or forced back into a position substantially flush with the outer contour or surface of the hip joint socket when they fail to encounter an attachment location at the bone.

BRIEF DESCRIPTION OF THE DRAWINGS

The invention will be better understood and objects other than those set forth above, will become apparent when consideration is given to the following detailed description thereof. Such description makes reference to the annexed drawings wherein throughout the various figures of the drawings there have been generally used the same reference characters to denote the same or analogous components and wherein:

FIG. 1 schematically illustrates a side view of an artificial hip joint socket according to the invention;

FIG. 2 schematically illustrates a view of the underside of the artificial hip joint socket of FIG. 1;

FIG. 3 schematically illustrates a section taken along the line III—III of FIG. 2;

FIG. 4 schematically illustrates an artificial hip joint socket grown into bone tissue in a side view taken in the direction of the arrow IV in FIG. 1 and partially cut away in section according to the line III—III in FIG. 2; and FIG. 5 schematically illustrates the hip joint socket according to the invention immediately prior to installation in prepared bone.

DETAILED DESCRIPTION OF THE PREFERRED EMBODIMENTS

Describing now the drawings, it is to be understood that to simplify the showing thereof only enough of the structure of the artificial hip joint socket has been illustrated therein as is needed to enable one skilled in the art to readily understand the underlying principles and concepts of the present invention. Turning now specifically to FIG. 1 of the drawings, the article illustrated therein by way of example and not limitation will be seen to comprise an artificial hip joint socket 1 made of a plastic material which is compatible with tissue and bone. An example of a suitable plastic material is polyethylene, which has been found to be suitable for such use.

This artificial hip joint socket 1 has a socket body which exhibits the form of a hollow hemisphere with a smoothly polished interior surface 2 and an outer surface 3 provided with grooves or channels 3a extending substantially parallel to an equatorial or opening plane 4 as well as several grooves or slots 3b extending substantially perpendicular thereto. The grooves or channels 3a and the grooves or slots 3b all serve to permit the bone matter to grow into the artificial hip joint socket 1 in order to ensure a firm union between the artificial hip joint socket 1 and the bone.

A metal ring 17 is seated in one of the grooves or channels 3a. This metal ring 17 permits the position of the hip joint socket 1 to be determined in a radiograph or X-ray image.

Four bores 6, 7, 8 and 9 extending skew to the equatorial or opening plane 4 permit the surgeon to fix the hip joint socket in the pelvic or hip bone by means of screws or dowels temporarily or permanently if he or she considers this necessary for any reason. A further bore 5 permits the hip joint socket 1 to be readily gripped by a surgical instrument.

Two anchor plugs or pins 10 and 11 are arranged on the outer surface 3 of the hip joint socket 1. The anchor plugs or pins 10 and 11 extend substantially parallel to one another but slightly obliquely upon the outer surface 3 of the hip joint socket 1. These anchor plugs or pins 10 and 11 are elastic, so that they can be inserted into corresponding bore holes in the bone even when the bore axes 15 of these bore holes form an angle of up to approximately 5° with the axes 16 of the anchor plugs or pins 10 and 11, as is shown in FIG. 5. Such a difference in angle between the axes 15 and 16 serves to prestress the anchor plugs or pins 10 and 11 such that the hip joint socket 1 is mechanically anchored in the inserted position. That is, the hip joint socket 1 is secured against rotation as well as falling out.

An optimum anchorage cannot be attained in all patients by such anchor plugs or pins 10 and 11, since local osseous conditions may vary. The artificial hip joint socket 1 according to the invention therefore comprises at least two supplementary barb-like anchor flaps 12 and 13 upon its outer surface 3, preferably arranged in the proximity of the edge region of the artificial hip joint socket 1. In the embodiment illustrated in FIG. 2 and 3, two supplementary anchor flaps 12 and 13 are provided in a mutually angular spaced relationship enclosing an angle in the range of 120° to 150°. In fact, each anchor flap 12 or 13 constitutes an undercut flange and the socket body of hip joint socket 1 contains two grooves 22 and 23 which are formed by an undercut and which are respectively associated with the anchor flaps 12 and 13. The two anchor plugs 10 and 11 are arranged substantially opposite the two anchor flaps 12 and 13. These anchor flaps 12 and 13, as can be seen from FIG. 4, effect an anchorage or retention in the prepared bone and secure the hip joint socket 1 against motion even when the anchor plugs or pins 10 and 11 are not able to provide adequate security for any reason. Thus, the surgeon can, in general, forego the use of screws or dowels for securing the hip joint socket 1 before growing in of the bone. These integrally formed resilient barb-like anchor flaps 12 and 13, which are cut-out from or undercut in the body of the hip joint socket, are advantageously deflected or forced back towards or in a position substantially flush with the outer surface or contour 3 of the hip joint socket when they fail to encounter an attachment location at the bone.

The same rules apply, both for medical indication and for surgical operations, in the insertion of such an artificial hip joint socket 1 as do for heretofore known artificial hip joint sockets with the inherent exception that it is possible, in consequence of the inventive anchor flaps 12 and 13 to omit the otherwise possibly requisite screws or dowels.

While there are shown and described present preferred embodiments of the invention, it is to be distinctly understood that the invention is not limited thereto, but may be otherwise variously embodied and practiced within the scope of the following claims.

Accordingly, what I claim is:

1. A plastic artificial hip joint socket for adhesive-free installation, comprising:
   a socket body having an outer surface defining an equitorial plane;
   two anchor plugs protruding from said outer surface; and
   at least two supplementary barb-like anchor flaps each of which is integrally formed with said socket body upon said outer surface by an undercut, which obliquely extends beneath said outer surface in a direction away from said equitorial plane defined by said socket body, and extends at an inclination relative to a line drawn tangent to said outer surface of said socket body for anchoring said socket body without the requirement of additional securing means, wherein;
   said barb-like anchor flaps are formed of a resilient plastic material enabling said barb-like anchor flaps to be deformed back towards the outer surface of the socket body so as to be flush with the surface of said socket body when said barb-like anchor flaps fail to encounter an attachment location at the bone;
   each said barb-like anchor flap constituting an undercut flange forming a groove positioned between said undercut flange and said socket body, whereby said undercut flange is able to deform into said groove, enabling said barb-like anchor flaps to be flush with the surface of said socket body.

2. A plastic artificial hip joint socket for adhesive-free installation, comprising:
   a socket body having an outer surface;
   two anchor plugs protruding from said outer surface;
   at least two supplementary barb-like anchor flaps integrally formed upon said outer surface and anchoring said socket body without the requirement of additional securing means;
   said barb-like anchor flaps being formed of a resilient plastic material enabling said barb-like anchor flaps to be deformed back towards the outer surface of the socket body when said barb-like anchor flaps fail to encounter an attachment location at the bone;
   each said barb-like anchor flap constituting an undercut flange forming a groove located between said undercut flange and said socket body, and;
   said undercut flanges of said barb-like anchor flaps being deformed back into said grooves into a position substantially flush with the outer surface of the socket body when said barb-like anchor flaps fail to encounter an attachment location at the bone.

3. A plastic artificial hip joint socket for adhesive-free installation, comprising:
   a socket body having an outer surface and an edge region adjacent an equitorial plane defined by said socket body;
   two anchor plugs protruding from said outer surface; and
   at least two supplementary barb-like anchor flaps each of which is integrally formed with said socket body upon said outer surface in proximity to said edge region by an undercut, which obliquely extends beneath said outer surface of said socket body and in a direction away from said equitorial plane defined by said socket body, and extends at an inclination relative to a line drawn tangent to said outer surface of said socket body enabling said barb-like anchor flaps to be deformed back toward said socket body so as to be flush with the surface of said socket body when said barb-like anchor flaps fail to encounter an attachment location at the bone.

4. The plastic artificial hip joint socket as defined in claim 3, wherein:
   each said barb-like anchor flap constituting an undercut flange forming a groove positioned between said undercut flange and said socket body, whereby said undercut flange is able to deform into said groove, enabling said barb-like anchor flaps to be flush with the surface of said socket body.

5. A plastic artificial hip joint socket for adhesive-free installation, comprising:
   a socket body having an outer surface and an edge region;
   two anchor plugs protruding from said outer surface;
   at least two supplementary barb-like anchor flaps integrally formed upon said outer surface in proximity to said edge region;

said barb-like anchor flaps being formed of a resilient plastic material enabling said barb-like anchor flaps to be deformed back towards the outer surface of the socket body when said barb-like anchor flaps fail to encounter an attachment location at the bone;

each said barb-like anchor flap constituting an undercut flange forming a groove located between said undercut flange and said socket body said undercut flanges of said barb-like anchor flaps being deformed back into said grooves into a position substantially flush with the outer surface of the socket body when said barb-like anchor flaps fail to encounter an attachment location at the bone.

* * * * *

UNITED STATES PATENT AND TRADEMARK OFFICE
CERTIFICATE OF CORRECTION

PATENT NO. : 4,685,923

DATED : August 11, 1987

INVENTOR(S) : Robert Mathys

It is certified that error appears in the above-identified patent and that said Letters Patent is hereby corrected as shown below:

The title page should be deleted to appear as per attached title page.

On Figure 3 of the drawings insert --No. 22-- and --No. 23-- as shown on the attached sheet.

Column 1, line 4, after "application" delete "is".

Signed and Sealed this

Nineteenth Day of April, 1988

Attest:

DONALD J. QUIGG

*Attesting Officer*     *Commissioner of Patents and Trademarks*

United States Patent [19]

Mathys

[11] Patent Number: 4,685,923
[45] Date of Patent: Aug. 11, 1987

[54] HIP JOINT SOCKET
[75] Inventor: Robert Mathys, Bettlach, Switzerland
[73] Assignee: Robert Mathys Co., Bettlach, Switzerland
[21] Appl. No.: 837,891
[22] Filed: Mar. 10, 1986

Related U.S. Application Data

[63] Continuation-in-part of Ser. No. 689,572, Jan. 7, 1985, abandoned.

[30] Foreign Application Priority Data

Jan. 11, 1984 [CH] Switzerland ............................ 121/84

[51] Int. Cl.[4] ................................................ A61F 2/34
[52] U.S. Cl. ................................................... 623/22
[58] Field of Search ..................... 623/20, 21, 22, 23; 128/92 C, 92 CA

[56] References Cited

FOREIGN PATENT DOCUMENTS

| 0058753 | 9/1982 | European Pat. Off. | 623/22 |
|---|---|---|---|
| 2807289 | 8/1979 | Fed. Rep. of Germany | 623/22 |
| 2857297 | 2/1980 | Fed. Rep. of Germany | 623/22 |
| 2225924 | 12/1974 | France | 623/22 |

Primary Examiner—Richard J. Apley
Assistant Examiner—David J. Isabella
Attorney, Agent, or Firm—Werner W. Kleeman

[57] ABSTRACT

An artificial hip joint socket made of plastic is intended to be installed in the pelvic bone without bone cement. The hip joint socket comprises a ribbed outer surface which permits good engagement of the bone tissue as well as two anchor plugs protruding from the outer surface which are intended to be inserted into corresponding bores in the bone. The angle which the plugs form with the socket surface deviate from the angle which the bores form with the socket surface by about 5° in order to effect a predetermined prestressing action which restrains the hip joint socket in position. Furthermore, the hip joint socket comprises at least two barb-like anchor flaps on its outer surface which either lie opposite one another or mutually include an angle of between 120° and 150°. A good seating of the hip joint socket in the bone is ensured by these flaps even immediately after insertion of the hip joint socket. Thus, even if the anchor plugs offer insufficient retention for any reason, the employment of screws or dowels can be completely or partially foregone.

5 Claims, 5 Drawing Figures

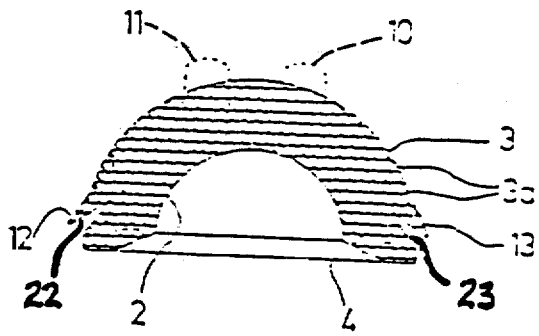

UNITED STATES PATENT AND TRADEMARK OFFICE
CERTIFICATE OF CORRECTION

PATENT NO. : 4,685,923

DATED : August 11, 1987

INVENTOR(S) : Robert Mathys

It is certified that error appears in the above-identified patent and that said Letters Patent is hereby corrected as shown below:

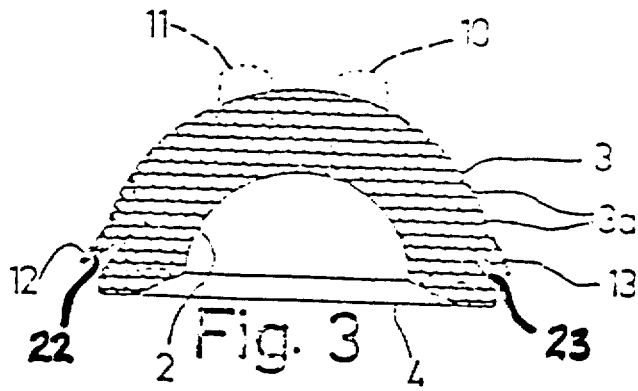

Fig. 3